United States Patent [19]

Lee et al.

[11] Patent Number: 5,597,780
[45] Date of Patent: Jan. 28, 1997

[54] LOW VOLATILITY FORMULATIONS OF MICROENCAPSULATED CLOMAZONE

[75] Inventors: Fui-Tseng H. Lee, Princeton; Paul Nicholson, Trenton, both of N.J.

[73] Assignee: FMC Corporation, Philadelphia, Pa.

[21] Appl. No.: 531,499

[22] Filed: Sep. 21, 1995

Related U.S. Application Data

[63] Continuation-in-part of Ser. No. 340,699, Nov. 16, 1994, abandoned.

[51] Int. Cl.$^6$ ............................ A01N 25/28; A01N 43/80
[52] U.S. Cl. ........................... 504/271; 71/DIG. 1
[58] Field of Search ................................ 504/271, 116; 71/DIG. 1

[56] References Cited

U.S. PATENT DOCUMENTS

| | | | |
|---|---|---|---|
| 3,577,515 | 5/1971 | Vandegaer | 424/32 |
| 4,280,833 | 7/1981 | Beestman et al. | 71/100 |
| 4,497,793 | 2/1985 | Simkin | 424/32 |
| 4,936,901 | 6/1990 | Surgant, Sr. et al. | 71/92 |
| 5,006,161 | 4/1991 | Hässlin et al. | 71/118 |

*Primary Examiner*—S. Mark Clardy
*Attorney, Agent, or Firm*—H. Robinson Ertelt; Robert M. Kennedy

[57] ABSTRACT

An herbicidal composition containing from 1 to 4 pounds of clomazone per gallon of formulation and having a clomazone volatility less than fifty percent of that of an emulsifiable concentrate containing four pounds of clomazone per gallon of formulation is prepared by the interfacial reaction of polymethylene polyphenyl isocyanate with a polyfunctional amine selected from ethylenediamine, diethylenetriamine, triethylenetetramine, 1,6-hexanediamine, and their mixtures in an aqueous phase optionally containing from 0.05 to 0.25 weight percent of a xanthan gum viscosity modified/stabilizer. Several such formulations and the method of their preparation are described.

14 Claims, No Drawings

LOW VOLATILITY FORMULATIONS OF MICROENCAPSULATED CLOMAZONE

This is a continuation-in-pad of Ser. No. 340,699, filed Nov. 16, 1994, abandoned.

The present invention relates to formulations of clomazone having reduced volatility relative to conventional emulsifiable concentrates of clomazone. In particular it relates to microencapsulated formulations of clomazone in which the clomazone is encapsulated in a shell of polyurea.

Clomazone, the common name for 2-(2-chlorophenyl) methyl-4,4-dimethyl-3-isoxazolinone, a highly effective herbicide, is also highly volatile, so much so that clomazone applied to the soil in a target area may move to adjacent area s and there cause discoloration, most typically whitening or some degree of bleaching, of a variety of crops, trees, or decorative plants. While this bleaching, indicative of the mode of action of the herbicide, may be temporary when plants are exposed to sufficiently low concentrations, it is unwelcome, even when it does not result in the destruction of the plant. Accordingly, the label for the use of Command® 4 EC Herbicide, an emulsifiable concentrate formulation in commercial use that contains four pounds of clomazone per gallon of formulation, lists a number of restrictions on how the product is to be used, including weather conditions, spray volume and pressure, and distance from areas where plants are in commercial production. For example, for preemergent applications clomazone is not to be applied within 1,500 feet of commercial fruit, nut, or vegetable production or commercial greenhouses or nurseries. Clearly, this is a severe limitation on the use of an herbicide.

It is the purpose of the present invention to reduce the volatility of clomazone formulations, so that problem of off-site injury is significantly reduced, i.e., by at least fifty percent, while maintaining a satisfactory level of herbicidal activity in the target area.

Attempts to prepare formulations of encapsulated clomazone by the general methods known to the art, including polyamide shells as well as polyurea, frequently resulted in formulations that not only gave little or no reduction in volatility, but had poor physical characteristics, e.g., undesirable agglomeration of the capsules or separation of phases. Perhaps one factor accounting for the difficulty in preparing satisfactory formulations is the significant water solubility of clomazone. No reports of formulations of encapsulated clomazone have been found.

It has now been found that encapsulated formulations of clomazone for which the volatility is reduced to fifty percent or less than that of the commercially available Command® 4 EC emulsifiable concentrate of clomazone, and which retain a satisfactory level of herbicidal activity, can be prepared, provided that the isocyanate and amine moieties that are to form the polyurea shell wall are carefully selected.

The process of the invention involves the following steps: (a) providing an aqueous phase containing an emulsifier, preferably a partially hydrolyzed polyvinyl alcohol; an antifoam agent, and optionally a xanthan gum viscosity modifier/stabilizer; (b) providing a water immiscible phase consisting of clomazone and polymethylene polyphenyl isocyanate, with or without a hydrocarbon solvent; (c) emulsifying the water immiscible phase in the aqueous phase to form a dispersion of water-immiscible droplets throughout the aqueous phase; (d) agitating the dispersion while adding to it, either neat or in aqueous solution, ethylenediamine, diethyltriamine, triethylenetetramine, 1,6-hexanediamine, or a mixture of the polyfunctional amines, thus forming a polyurea shell wall around the water-immiscible droplets. Once the microcapsules are formed, the suspension is cured by moderate heating, after which one or more stabilizing agents, such as propylene glycol, xanthan gum, smectite clay, or an ionic dispersing agent such as a sulfonate of an alkyl napthalene, may be added, as is well-known in the art. It has also been found that adjusting the pH of the formulation from mildly acidic to mildly alkaline conditions, such as a range of from 6.5 to 9.0, e.g., pH 8.9, results in a formulation having improved storage stability. The addition of these materials after encapsulation and curing to adjust viscosity and suspensibility is not seen to have any effect on the loss of clomazone through volatility or on the herbicidal efficacy of the formulation.

The aqueous phase will ordinarily contain 0.3 to 3.0, preferably 0.8 to 2.0, weight percent of one or more emulsifiers, e.g., polyvinyl alcohol, 0.05 to 0.20, preferably 0.06 to 0.15, weight percent of the xanthan gum viscosity modifier/stabilizer, if it is used, and 0.1 to 1.0, preferably 0.4 to 0.9, weight percent of the antifoam agent.

The water-immiscible phase will ordinarily consist of 60 to 85, preferably 65 to 77, weight percent of clomazone, an amount of polymethylene polyphenyl isocyanate (PMPPI) such that the ratio of clomazone to PMPPI is in the range of 1:1 to 6:1, preferably 4.5:1 to 4.8:1, and an aromatic hydrocarbon solvent for the two solutes. However, use of solvent is optional in the preparation of formulations containing more than about two pounds of clomazone per gallon of formulation. In such preparations a small amount of solvent may still be used to depress the melting point.

The amine solution will ordinarily contain 10 to 100, preferably 30 to 40, weight percent of ethylenediamine, diethylenetriamine, triethylenetetramine, 1,6-hexanediamine, or preferably a mixture of the polyfunctional amines, with ethylene diamine being used only in a mixture.

The emulsification step requires high shear mixing to give small droplets of the immiscible phase. Factors that influence droplet size, which determines the eventual size of the microcapsules, as well as the stability of the emulsion, include speed and length of mixing, the type and amount of surfactant, solvent, temperature, and viscosity, as well as the xanthan gum, when used. Selection of the appropriate microcapsule size to achieve the purposes of the invention requires a balance between competing factors. In general, increasing microcapsule size decreases volatility, but also decreases suspensibility of the particles, while decreasing size yields better suspensibility, but higher volatility. For the purposes of the present invention the average size of the microcapsules is 5 to 50 microns, preferably 5 to 30 microns. The operating conditions to yield microcapsules of a desired size will depend on the emulsifying equipment used, and the adjustment to determine the proper conditions is well within the skill of the art.

In contrast to the conditions of the emulsification step, agitation during the amine addition should be gentle. Stirring is continued while the suspension is cured by heating to a temperature of 35 to 60, preferably 45° to 50° C., for 3 to 10, preferably 4 to 5, hours.

The amounts of post encapsulation additives to be added typically would be selected from one or more of 0.75 to 6.5 wt. % propylene glycol, 0.05 to 0.30 wt. % xanthan gum, 0.25 to 0.50 wt. % smectite clay, and 0.5 to 6.0 wt. % one or more surfactants, each weight percent relative to the weight of the formulation after addition of the stabilizers.

The formulations of the present invention are prepared by the methods exemplified in the following examples.

EXAMPLE 1

Preparation of a Clomazone 1.5 Pound/Gallon
Capsule Suspension (5 CS) Formulation
(Formulation A).

A stock solution of aqueous 20% (weight/weight) partially hydrolyzed polyvinyl alcohol having an average molecular weight of 13,000 to 23,000 (Airvol® 203) was prepared by stirring and heating the appropriate amounts of polyvinyl alcohol and water at about 80°–90° C. for one hour. The cooled solution was stored for later use.

In a one-liter stainless steel beaker were placed 20.0 grams of the aqueous 20% polyvinyl alcohol solution prepared above, 1.8 grams of 100 % of a polydimethyl siloxane antifoam agent (Dow Corning® 1500), 15.0 grams of aqueous 2% xanthan gum (Kelzan® M), and 400.0 grams of water. After this mixture was mixed for 20 seconds at high speed in a high-shear mixer, a pre-blended solution of 140.0 grams of clomazone, 30.0 grams of polymethylene polyphenyl isocyanate (PMPPI, Mondur® MR), and 30.0 grams of petroleum solvent (a mixture of $C_9$–$C_{15}$ aromatic, naphthalene-depleted, hydrocarbons, flash-point 95° C., Aromatic 200 ND) was added, and the mixture was emulsified in the high shear mixer for five minutes. The mixture was then placed in a one-liter jacketed resin flask with the jacket pre-heated to 50° C. The mixture was stirred at a moderate speed with an air-powered stirrer, and a solution of 19.0 grams of triethylenetetramine (TETA) in 35.0 grams of water was added in one portion. The mixture was then stirred at 50° C. for four hours. After this time, 2.5 grams of a smectite clay containing magnesium aluminum silicate, titanium dioxide, and cristobalite (Veegum® Ultra), and 15.0 grams of aqueous 2% xanthan gum (Kelzan® M) were added to stabilize the formulation. The formulation was then stirred for about one hour and stored for later use.

The formulations described in Tables 1 and 2 were prepared in this manner.

EXAMPLE 2

Large Scale Preparation of a Clomazone 2.0
Pound/Gallon Capsule Suspension (2.0 CS)
Formulation (Formulation E-1)

A solution of 5.24 pounds of polyvinyl alcohol (Airvol 203), 2.38 pounds of an aqueous solution of 20% polydimethyl siloxane antifoam agent (Dow Corning® 1520), and 0.21 pound of xanthan gum viscosity modifier/stabilizer (Kelzan® S) in 284.20 pounds of water was placed in a 500 gallon stainless steel vessel, and stirred at 80° C. for one hour. After this time the solution was cooled to 20° C. and placed in an 80 gallon batch homogenizer. With the homogenizer in operation, a pre-blended solution of 161.34 pounds of technical clomazone, 34.75 pounds of polymethylene polyphenyl isocyanate (PMPPI, Mondur® MR), and 34.75 pounds of petroleum solvent (a mixture of $C_9$–$C_{15}$ aromatic hydrocarbons, flash-point 95° C., Aromatic 200) was fed by gravity into the homogenizer during a 15 to 90 second period. The mixture was homogenized for two to three minutes. Upon completion of the homogenization, the mixture was placed in a jacketed reactor with the jacket pre-heated to 50° C. To the jacketed reactor was added, over a period of 30 seconds, an amine mixture consisting of 10.97 pounds of triethylenetetramine (TETA) and 10.97 pounds of 1, 6-hexanediamine (HDA). After the amine addition was completed, the mixture was cured with agitation at 25° C. to 50° C. during a four hour period. At the end of the curing period, 35.70 pounds of propylene glycol and 1.19 pounds of xanthan gum were added to stabilize the formulation. The formulation was then cooled to below 30° C. and stored for later use. It had a viscosity of 1870 cps and a suspensibility of 82%. Both formulations described in Tables 3 and 4 were prepared in the manner of Example 2. Formulation A-1 is a larger scale version of Formulation A, and Formulation E-1 is a larger scale version of Formulation E.

Formulation P, a three pound per gallon formulation, the components of which are given in Tables 3 and 4, was prepared by the method of Example 2. In this preparation 0.133 pound of the sodium sulfonated naphthalene condensate was added to the aqueous phase during its preparation. The post encapsulation additives, including the remainder of the sodium sulfonated naphthalene condensate, was added after the curing period at about 35° C., while the formulation continued to mix and cool to ambient temperature. The hydrochloric acid was then added to bring the pH from 10.8 to 8.9.

The currently preferred practice, after the curing step, is to continue stirring the formulation until the temperature reaches about 35° C., and then to add the hydrochloric acid to bring the pH to about 7.8. The post encapsulation additives, including the remainder of the sodium sulfonated naphthalene condensate, is added, and stirring of the formulation is continued for about 30 minutes to give a homogeneous mixture.

In subsequent preparations of Formulation E by the method of Example 1, certain refinements in the procedure have been found advantageous. Adjusting the pH of the aqueous solution to 4 reduced the undesirable reaction between PMPPI and water, as did cooling the solution to 8°–10° C. Preparations have also been carried out with the clomazone solution and the amine solution, as well as the initial aqueous solution, all cooled to 8°–10° C. However, when there is no solvent in the water-immiscible phase, low temperatures are not used to avoid freezing the clomazone.

Other formulations prepared by the method of Example 1, but differing from the formulations of the invention in the components of either the isocyanate-or amine-containing phase, proved to be unsatisfactory in controlling the volatility of clomazone or in the physical stability of the formulation. The compositions of representative unsatisfactory formulations are given in Table 5. Three of these formulations failed to control the volatility of clomazone adequately, as will be shown below. Formulation O was too viscous (6360 cps).

Formulation L is the same as Formulation A of the present invention, except that the polymethylene polyphenyl isocyanate (PMPPI) was replaced with toluene diisocyanate (TDI). TDI is more reactive in water than PMPPI, which causes undesirable side-reactions leading to foaming in the emulsification step of the preparation of this formulation.

Formulation M was an attempt to copy the formulation used successfully in an effective, four pound/gallon, capsule suspension formulation of an insecticide, substituting clomazone for the insecticide. The microcapsules produced were too small, and here, too, TDI caused foaming problems.

Formulation N is the same as Formulation A of the present invention, except that the xanthan gum viscosity modifier/stabilizer is not used in the emulsification step. Batches of Formulation N prepared in this way gave microcapsules that not only are somewhat small, but are not uniform in size and tend to aggregate. Moreover, the formulation has poor physical stability, resulting in phase separation.

That attaining the desired combination of reduced volatility, physical properties, and efficacy is not achieved simply by following the prior art is shown by two additional preparations. Formulations V and W were prepared by the method of U.S. Pat. No. 4,280,833, Example 8. The composition of these formulations is given in Table 5a. Both formulations separated on standing, forming in the bottom of the container a hard-packed layer, which could be redispersed by shaking. Each gave at least as much release of clomazone as the standard Command® 4 EC Herbicide, when subjected to the laboratory volatility test described below.

The average size of the microcapsules of formulations of the invention, as well as the unsatisfactory formulations, is given in Table 6.

Volatility Studies

Laboratory tests for the volatility of capsule suspension (CS) formulations of clomazone were carried out in the following manner. Sufficient unsterilized topsoil to conduct the test was passed twice through a 14-mesh sieve to remove large particles and debris. The fine particles were then removed through a 30-mesh sieve, leaving behind topsoil of intermediate-sized particles. This intermediate-sized topsoil, 240 grams, was spread uniformly to a thickness of about one to two millimeters over an area of about 27.9 cm.×41.3 cm in a tray measuring 32.4 cm×45.7×1.9 cm. The topsoil was then sprayed from an overhead track sprayer calibrated to deliver 20 gallons of water per acre. The spray mix consisted of sufficient clomazone test formulation to provide 0.0712 gm of active ingredient in 20 mL of water. In this manner the clomazone test formulation was applied to the soil at a rate of 1.0 kg a.i. (active ingredient)/ha. Immediately after treatment, the soil was enclosed in a glass jar, where it remained briefly until used.

For each clomazone test formulation, four 22 mm×300 mm glass chromatography columns, each containing a coarse sintered glass barrier at the bottom, were connected through their bottom ends to a multi-port air manifold, which delivered equal air pressure simultaneously to a number of columns. In each of the four columns was placed 59 gms of the treated topsoil, which filled about 200 mm of the column length. In the top of each column was then placed a polyurethane foam plug designed to fit inside a 21 to 26 mm diameter tube. As soon after the soil treatment as the columns could be set up, a slow stream of air (0.75–1.00 liter per minute per column) from the multi-port air manifold was passed through the soil in each column, causing the volatilized clomazone to collect on the polyurethane foam plug. The time between the soil treatment and the start of the air flow was about one hour. The air flow was continued for about 18 hours.

Following the 18 hour collection period, the polyurethane foam plug from each column was placed in a 20 mL plastic syringe. The polyurethane foam plug was thoroughly extracted by drawing 15 mL of methanol into the syringe and through the plug, forcing the methanol extract into a beaker, and repeating the process several times. A 0.04 mL aliquot of the 15 mL sample was diluted with 0.96 mL of methanol and 1.0 mL of water. A 0.1 mL aliquot of this solution was analyzed for clomazone content using an enzyme-linked immunosorbent assay (ELISA), a method reported by R. V. Darger et al. (J. Agr. and Food Chem., 1991, 39, 813–819). The total clomazone content of the foam plug, expressed in micrograms, of each sample was recorded and compared to the clomazone content of the sample from the standard, Command® 4 EC Herbicide.

The test results, given in Table 7, show that the CS formulations of the present invention are effective in reducing the amount of clomazone lost by volatility. While all of the formulations listed gave a significant reduction in volatility, the results for Formulations E and F, prepared from mixtures of TETA and HDA, are particularly noteworthy, losing only 8% and 10%, respectively, as much clomazone as was lost from the standard 4 EC. The 2.0 lb/gal formulations made from the single polyfunctional amines, Formulation B from TETA and Formulation D from HDA, each lost more than twice as much clomazone as did the formulations prepared from mixtures. Also, Formulations G and H each had less volatility loss than that of either HDA or DETA alone (Formulations D and K). Accordingly, in the preparation of the formulations of this invention, the use of mixtures of DETA or TETA or both with HDA, particularly in ratios of 3:1 to 1:3, give unexpectedly superior reduction of volatility. Mixtures of TETA and EDA give volatility lower than that of TETA alone. However, it should be noted that Formulation P, a 3 lb/gal formulation, with DETA alone, gave as much reduction in volatility as Formulations G and H.

The unsatisfactory formulations L, M, and N are clearly far less effective in reducing the volatility of clomazone. The high volatility loss for Formulation L (91% of that lost by the standard clomazone 4.0 EC) suggests that the polymeric walls formed from triethylenetetramine (TETA) and TDI are too permeable, allowing the clomazone to volatilize and the walls formed from PMPPI and TETA or PMPPI in combination with TETA and 1,6-hexanediamine (HDA) are much less permeable, so that clomazone loss from volatility is much reduced. Formulation M, which gives excellent results when the active ingredient is a less water-soluble insecticide, is totally unacceptable for clomazone, giving volatility equal to that of the standard clomazone 4.0 EC. The difference between Formulations A and N in reducing the loss of clomazone through volatility is particularly surprising, inasmuch as the only difference is the absence of xanthan gum in the aqueous solution prior to encapsulation in Formulation N. The function of xanthan gum seems unpredictable, however, since the only difference between Formulations K and O is the presence of xanthan gum in the aqueous solution prior to encapsulation in K. These two formulations have the same volatility loss, but the viscosity of Formulation K is 3640 cps, while that of O is 6360! No discernible difference has been found between Kelzan® M and Kelzan S xanthan gum in the aqueous phase prior to encapsulation in their effect on the formulations.

Formulations V and W, based on the an earlier patent, were no better than the 4 EC formulation in controlling volatility.

Tests to determine the volatility of clomazone CS formulations in the field relative to that of the standard, Command® 4 EC Herbicide were carried out as follows. One trial on Formulation A-1 was conducted in a field of two-week old sunflowers, a plant species susceptible to clomazone. Plots were established on a 12×14 meter grid. Each plot was prepared by removing the sunflower seedlings and other vegetation from areas about 60 cm in diameter located at the intersections of the grid lines. The grid lines were 12 meters apart in one direction and 14 meters apart in the perpendicular direction. The edge of one replicate was at least 12 meters from the edge of the next replicate, a distance sufficient to prevent interference between replicates. Over each plot where the soil was exposed was placed a 60 cm diameter, open-ended barrel that was lined with a plastic sleeve fashioned from a trash can liner. Each plot was sprayed with 10–15 mL of an aqueous dispersion containing 0.12 gram of active ingredient. To minimize the drift of clomazone, the spraying was conducted inside the barrel using a hand-held sprayer. Upon completion of each application, the barrel was left in place, and the top was covered for about two to three minutes to allow the spray to settle to the soil surface. The barrel was then removed, leaving each plot open to ambient conditions. There were three to four replicates for each test formulation. To prevent cross-contamination, the plastic sleeve was replaced before applying each new test formulation. The test was evaluated at seven days after treatment by measuring the distance from the center of each plot to, first, the most distant point where discoloration of the sunflowers could be found, then at 45° intervals around the center of the plot. The area of discoloration of the sunflowers was calculated, and the area of the direct treatment was subtracted to provide the area affected by the volatility of clomazone.

A second test on Formulation A-1 was carried out in the same manner in a second field of sunflowers, this time with a 44 cm barrel and on a 14×14 meter grid. The total areas affected by clomazone movement from each test site for each test formulation and the standard clomazone 4.0 EC formulation were determined. From these data a percent reduction of area discolored by clomazone as compared to the standard Command® 4 EC was calculated for each test formulation.

A third test, this time with Formulation P, was a series of tests, carried out in different geographic locations having different environmental and soil conditions. At each location a three acre plot was planted with sunflowers. The clomazone formulations were applied to a 10'×10' bare ground plot when the sunflowers had reached the 2–6 leaf stage. Prerequisite conditions for application were that the soil be moist, but not saturated, to facilitate volatilization. Evaluations were made 7–10 days after application and 10–14 days after the first significant rainfall event by means of the same general method described for the first test. The areas given are totals for all sites; the percent reduction is an average of those from all sites. The test results, given in Table 8, show that Formulation A-1 reduced by one half the area affected by clomazone compared to Command 4 EC, and Formulation P was significantly more effective in reducing volatility.

Efficacy Studies

Seeds of barnyardgrass (*Echinochloa crusgalli*), giant foxtail (*Setaria faberi*), yellow foxtail (*Setaria lutescens*), shattercane (*Sorghum bicolor*), and velvetleaf (*Abutlion theophrasti*) were planted in a 25 cm×15 cm×7.5 cm fiber flat containing topsoil. Each species was planted as a single row in the flat, which contained five rows. There were four replicate flats of plants for each rate of application of test formulation. Stock dispersions of each of the test formulations were prepared by dispersing a sufficient amount of formulation to provide 0.0356 gram of active ingredient in 40 mL of water. From the stock dispersion 20 mL was removed and serially diluted with 20 mL of water to provide application rates of 0.25, 0.125, 0.0625, 0.0313, 0.0156, and 0.0078 kg. a.i./ha. The dispersions of test formulation for each rate of application were then sprayed onto the surface of the soil by a track-sprayer in a sprayhood. Flats were also sprayed as above with the same rates of the standard Command® 4 EC Herbicide. Untreated controls were also included in each test. Upon completion of the spraying the flats were placed in a greenhouse, where they were maintained for fourteen days. After this time the test was visually evaluated for percent weed control. The percent weed control data for each test formulation and the Command 4 EC Herbicide formulation was subjected to regression analysis to determine the rate of application that would provide 85% weed control ($ED_{85}$) of each of the weed species. From these data the relative potencies of the test formulations (the relative potency of the Command 4 EC Herbicide is 1.0) were determined by means of the following ratio:

$$\text{Formulation Relative Potency} = \frac{\text{Formulation } ED_{85}}{\text{Command Herbicide } ED_{85}}$$

The test results shown in Table 9 show relatively poor performance for Formulation E in the greenhouse. As shown below, performance of Formulation E in the field was excellent. The reason for the difference between greenhouse and field performance is not understood. However, the greenhouse performance of Formulation P was excellent, as was performance in the field, as shown below."

In a field test of the efficacy of Formulation A-1 the test formulations were sprayed onto the surface of the soil (preemergence) at an application rate of 1.0 pound a.i./acre in 12.7×30 foot plots planted with cotton and weed seeds. There were four replicate plots for each formulation tested. The test formulation was applied by means of a backpack sprayer, equipped with flat fan spray nozzles, at a delivery volume of 15–20 gallons/acre and at a spray pressure of 28–30 psi. The plots were evaluated for percent weed control at 15 and 30 days after emergence of the plant species in the test. The cotton plants were evaluated for bleaching, stunting, and stand reduction. Test results, given in Table 10, show this CS formulation to be slightly less effective against three of the four test species and essentially equivalent to the 4 EC in effects on cotton. (The similarity in effect on cotton is not unexpected, since this test is the result of direct application and does not involve movement to an adjacent site.)

In a field test of Formulation E the test formulations were sprayed onto the surface of the soil (preemergence) at application rates of 0.125, 0.25, and 0.5 pound a.i./acre in 6.7×12 foot plots planted with eight different plant species. There were four replicate plots for each formulation tested. The test formulations were applied using a backpack sprayer, equipped with four flat fan spray nozzles, at a delivery volume of 20 gallons/acre and at a spray pressure of 25 psi. The plots were evaluated for percent control 20 days after treatment. The data in Table 11 show that this CS formulation at 0.5 pound active ingredient per acre is giving commercial control, defined as at least 80 to 85 percent control of all species, everywhere the standard is giving commercial control, except for shattercane at 0.5 lb/A, which falls slightly below the percentage goal for control.

Table 12 reports results of a field test of Formulation P and the 4 EC formulation in which both formulations were applied at 0.88 lb/A, preemergence. It is apparent that in most cases where the 4 EC formulation is giving commercial control, Formulation P is also. Again, the effect of the encapsulated formulation P on cotton is negligible.

Table 13 reports another field test of Formulation P, again applied preemergence, that shows that at 0.5 lb/A the encapsulated formulation is controlling all species except shattercane.

As noted above, the stabilizers added after encapsulation and curing are thought to have no effect on the volatility or the efficacy of the formulation. They are added to stabilize the formulation and adjust the viscosity. It is prefered that each formulation of this invention have a suspensibility of greater than 70%, a viscosity of 1700 to 3800 cps, and a 100 mesh wet screen analysis of greater than 99.95%.

It is understood that there may be variations from the specific embodiments described herein without departing from the spirit or concept of the present invention as defined in the claims. Included in such variations are mixtures in which the encapsulated clomazone of this invention is part of a mixture with one or more other herbicides, e.g., flumeturon or sulfentrazone, whether or not encapsulated.

TABLE 1

Preparation of Clomazone Capsule Suspension (CS) Formulations
(Components and Amounts)

| Formulation | Weight (grams) | | | | | |
|---|---|---|---|---|---|---|
| (lb/gal) | A (1.5) | B (2.0) | C (1.5) | D (2.0) | E (2.0) | F (2.0) |
| Component | | | | | | |
| Aqueous Solution | | | | | | |
| Water | 430.7 | 493.00 | 430.70 | 493.00 | 493.00 | 493.00 |
| PVA | 4.0 | 4.58 | 4.00 | 4.58 | 4.58 | 4.58 |
| Xanthan Gum (a.i.) | 0.3 | 0.35 | 0.30 | 0.35 | 0.35 | 0.35 |
| Antifoam (a.i.) | 1.8 | 2.06 | 1.80 | 2.06 | 2.00 | 2.06 |
| Isocyanate Solution | | | | | | |
| Clomazone | 140.0 | 280.00 | 140.00 | 280.00 | 280.00 | 280.00 |
| Petroleum Solvent | 30.0 | 60.00 | 30.00 | 60.00 | 60.00 | 60.00 |
| PMPPI | 30.0 | 60.00 | 30.00 | 60.00 | 60.00 | 60.00 |
| Amine Solution | | | | | | |
| TETA | 19.0 | 38.00 | — | — | 19.00 | 9.50 |
| HDA | — | — | 19.00 | 30.00 | 19.00 | 28.50 |
| Water | 35.0 | 62.00 | 31.00 | 70.00 | 62.00 | 62.00 |
| Post Encapsulation Stabilizers | | | | | | |
| Smectite Clay in Water | 2.5 14.7 | — | — | — | — | — |
| Propylene Glycol | — | 19.60 | 9.00 | 18.00 | 9.00 | 18.00 |
| Xanthan Gum (a.i.) | 0.3 | 0.40 | 1.00 | 2.00 | 1.00 | 2.00 |

| | Weight (grams) | | | | |
|---|---|---|---|---|---|
| Formulation (lb/gal) | G (2.0) | H (2.0) | I (2.0) | J (2.0) | K (2.0) |
| Component | | | | | |
| Aqueous Solution | | | | | |
| Water | 493.00 | 493.00 | 493.00 | 493.30 | 493.00 |
| PVA | 4.6 | 4.6 | 4.58 | 4.58 | 4.58 |
| Xanthan Gum (a.i.) | 0.4 | 0.4 | 0.35 | — | 0.35 |
| Antifoam (a.i.) | 2.1 | 2.06 | 2.06 | 2.06 | 2.06 |
| Isocyanate Solution | | | | | |
| Clomazone | 280.0 | 280.00 | 280.00 | 280.00 | 280.00 |
| Petroleum Solvent | 60.0 | 60.00 | 60.00 | 60.00 | 60.00 |
| PMPPI | 60.0 | 60.00 | 60.00 | 60.00 | 60.00 |
| Amine Solution | | | | | |
| EDA | — | — | 7.6 | 7.6 | — |
| TETA | — | — | 30.4 | 30.4 | — |
| DETA | 11.20 | 19.00 | — | — | 38.00 |
| HDA | 19.00 | 19.00 | — | — | — |
| Water | 69.8 | 62.00 | 62.00 | 62.00 | 62.00 |
| Post Encapsulation Stabilizers | | | | | |
| Smectite Clay in Water | — | — | — | — | — |

TABLE 1-continued

Preparation of Clomazone Capsule Suspension (CS) Formulations
(Components and Amounts)

| Propylene Glycol | — | 41.00 | 19.60 | 19.60 | 19.60 |
| Xanthan Gum (a.i.) | — | 1.00 | 0.40 | 0.40 | 0.40 |

PVA - Airvol ® 203 polyvinyl alcohol.
Xanthan gum - Kelzan ® M and Kelzan S xathan gums differ in that S has been surface treated to improve ease of dispersion. M was used in all cases except post encapsulation in Formulations A, C, D, F, and H.
Antifoam - Dow Corning ® 1500 is 100% polydimethyl siloxane. Dow Corning 1520 is a 20% solution; amount shown is active ingredient (a.i.). 1500 was used in Formulations A and C; 1520 in the others.
Petroleum solvent - Aromatic 200, a mixture of $C_9$–$C_{15}$ aromatic hydrocarbons, flash point 95° C. That used in Formulation A was naphthalene depleted.
PMPPI - Mondur ® MR polymethylene polyphenyl isocyanate.
TETA - triethylenetetramline.
HDA - 1,6-hexanediamine.
Smectite clay - Veegum ® Ultra clay consisting of magnesium aluminum silicates with titanium dioxide and cristobalite present.
EDA - ethylenediamine.
DETA - diethylenetriamine.

TABLE 2

Clomazone Capsule Suspension (CS) Formulations
(Components and Weight/Weight Percents)

| Formulation | Percent (wt/wt) | | | | | |
|---|---|---|---|---|---|---|
| (lb/gal) | A (1.5) | B (2.0) | C (1.5) | D (2.0) | E (2.0) | F (2.0) |
| Component | | | | | | |
| Clomazone Encapsulating Polymer | 19.77 | 27.45 | 20.09 | 27.45 | 27.72 | 27.45 |
| PMPPI | 4.24 | 5.88 | 4.31 | 5.88 | 5.94 | 5.88 |
| HDA | — | — | 2.72 | 2.94 | 1.88 | 2.79 |
| TETA | 2.68 | 3.73 | — | — | 1.88 | 0.93 |
| Polyvinyl Alcohol | 0.56 | 0.45 | 0.57 | 0.45 | 0.45 | 0.45 |
| Petroleum Solvent | 4.24 | 5.88 | 4.31 | 5.88 | 5.94 | 5.88 |
| Polydimethyl Siloxane-Antifoam Agent | 0.25 | 0.20 | 0.26 | 0.20 | 0.20 | 0.20 |
| Xanthan Gum-Viscosity Modifier/Stabilizer | 0.08 | 0.07 | 0.19 | 0.23 | 0.13 | 0.23 |
| Propylene Gylcol Stabilizer | — | 1.92 | 1.29 | 1.77 | 0.89 | 1.77 |
| Smectite Clay-Viscosity Modifier | 0.35 | — | — | — | — | — |
| Water | 67.83 | 54.42 | 66.26 | 55.20 | 54.95 | 54.42 |
| Total | 100.00 | 100.00 | 100.00 | 100.00 | 100.00 | 100.00 |

| | Percent (wt/wt) | | | | |
|---|---|---|---|---|---|
| Formulation (lb/gal) | G (2.0) | H (2.0) | I (2.0) | J (2.0) | K (2.0) |
| Component | | | | | |
| Clomazone Encapsulating Polymer | 28.00 | 26.7 | 27.45 | 27.45 | 27.45 |
| PMPPI | 6.00 | 5.70 | 5.88 | 5.88 | 5.88 |
| EDA | — | — | 0.75 | 0.75 | — |
| TETA | — | — | 2.98 | 2.98 | — |
| DETA | 1.12 | 1.80 | — | — | 3.73 |

TABLE 2-continued

Clomazone Capsule Suspension (CS) Formulations
(Components and Weight/Weight Percents)

| | | | | | |
|---|---|---|---|---|---|
| HDA | 1.90 | 1.80 | — | — | — |
| Polyvinyl Alcohol | 0.46 | 0.44 | 0.45 | 0.45 | 0.45 |
| Petroleum Solvent | 6.00 | 5.70 | 5.88 | 5.88 | 5.88 |
| Polydimethyl Siloxane-Antifoam Agent | 0.21 | 0.20 | 0.20 | 0.20 | 0.20 |
| Xanthan Gum-Viscosity Modifier/Stabilizer | 0.04 | 0.13 | 0.07 | 0.04 | 0.07 |
| Propylene Gylcol Stabilizer | — | 4.67 | 1.92 | 1.92 | 1.92 |
| Water | 56.27 | 52.86 | 54.42 | 54.45 | 54.42 |
| Total | 100.00 | 100.00 | 100.00 | 100.00 | 100.00 |

TABLE 3

Large Scale Preparation of Clomazone CS Formulations
(Components and Amounts)

| | Weight (lbs) | | |
|---|---|---|---|
| Formulation (lb/gal) | A-1 (1.5) | E-1 (2.0) | P (3.0) |
| Component | | | |
| Aqueous Solution | | | |
| Water | 222.85 | 284.20 | 274.4 |
| PVA | 2.000 | 5.24 | 5.05 |
| Xanthan Gum | 0.300 | 0.21 | 0.22 |
| Antifoam | 0.900 | 2.38 | 4.30 |
| Isocyanate Solution | | | |
| Clomazone | 70.000 | 161.34 | 289.8 |
| Petroleum Solvent | 15.000 | 34.75 | 31.2 |
| PMPPI | 15.000 | 34.75 | 62.5 |
| Amine Solution | | | |
| TETA | 9.500 | 10.97 | — |
| HDA | — | 10.97 | — |
| DETA | — | — | 40.0 |
| Water | 17.500 | 40.50 | — |
| Post Encapsulation Additives | | | |
| Propylene Glycol | — | 35.70 | 39.8 |
| Xanthan Gum | — | 1.19 | 26.2* |
| Smectite Clay | 1.250 | — | — |
| Bactericide A[1] | 0.009 | — | — |
| Bactericide B[2] | 0.177 | — | — |
| Bactericide C[3] | — | — | 0.4 |
| Na Naphthalene Sulfonate[4] | — | — | 5.3 |
| Concentrated Aqueous Hcl | — | — | 22.33 |
| Amphoteric Surfactant[5] | — | — | 26.0 |

[1]Dowcide ® A (o-phenylphenate tetrahydrate)
[2]Legend ® MK (mixture of 2-methyl-4-isothiazolin-3-ones)
[3]Proxel ® (1,2-benzisothiazolin-3-one)
[4]Sodium salt of sulfonated naphthalene condensate
[5]Mirataine ™ H2C-HA (sodium lauriminodipropionate)
*as a 1.9 wt % dispersion.

TABLE 4

Large Scale Clomazone CS Formulations
(Components and Weight/Weight Percents)

| | Percent (wt/wt) | | |
|---|---|---|---|
| Formulation | A-1 | E-1 | P |
| Component | | | |
| Clomazone | 19.74 | 25.93 | 35.02 |
| Encapsulating Polymer | | | |
| PMPPI | 4.23 | 5.59 | 7.55 |
| HDA | — | 1.76 | — |
| TETA | 2.68 | 1.76 | — |
| DETA | — | — | 4.83 |
| Polyvinyl Alcohol | 0.56 | 0.84 | 0.61 |
| Petroleum Solvent | 4.23 | 5.59 | 3.77 |
| Polydimethyl Siloxane-Antifoam Agent | 0.25 | 0.38 | 0.53 |
| Xanthan Gum-Viscosity Modifier/Stabilizer | 0.09 | 0.23 | 0.09 |
| Propylene Gylcol Stabilizer | — | 5.74 | 4.81 |
| Smectite Clay-Viscosity Modifier | 0.37 | — | — |
| Bactericides | 0.05 | — | 0.05 |
| Na Naphthalene Sulfonate Condensate | — | — | 0.65 |
| Concentrated Aqueous Hcl | — | — | 2.70 |
| Amphoteric Surfactant | — | — | 0.94 |
| Water | 67.80 | 52.18 | 38.45 |
| Total | 100.00 | 100.00 | 100.0 |

TABLE 5

Unsatisfactory Clomazone CS Formulations
(Components and Weight/Weight Percents)

| | Percent (Wt/Wt) | | | |
|---|---|---|---|---|
| Formulation | L | M | N | O |
| Component | | | | |
| Clomazone | 20.38 | 30.43 | 20.38 | 27.45 |
| Encapsulating Polymer | | | | |
| PMPPI | — | — | 4.37 | 5.88 |
| TDI | 4.37 | 1.73 | — | — |
| TETA | 2.77 | — | 2.77 | — |
| DETA | — | 0.73 | — | 3.73 |
| EDA | — | 0.15 | — | — |
| Polyvinyl Alcohol | 0.58 | 2.72 | 0.58 | 0.45 |
| Petroleum Solvent | 4.37 | — | 4.37 | 5.88 |
| Polydimethyl Siloxane Antifoam Agent | 0.26 | 0.28 | 0.26 | 0.20 |
| Xanthan Gum Viscosity Modifier/Stabilizer | 0.04 | — | — | 0.04 |
| Propylene Glycol Stabilizer | — | — | — | 1.92 |
| Water | 67.23* | 63.96 | 67.27* | 54.45* |
| Total | 100.00 | 100.00 | 100.00 | 100.00 |

TDI is toluene diisocyanate
DETA is diethylenetriamine
EDA is ethylenediamine
*Ten mL of a 10% solution of xanthan gum in propylene glycol was added to stabilize the formulation after it was prepared.

TABLE 5a

Unsatisfactory Clomazone CS Formulations
(Components and Weight/Weight Percents)

|  | Weight (g) | | Percent (Wt/Wt) | |
|---|---|---|---|---|
| Formulation | V | W | V | W |
| Component | | | | |
| Clomazone | 300.0 | 300.0 | 34.9 | 49.0 |
| Encapsulating Polymer | | | | |
| PMPPI | 22.5 | 22.5 | 2.6 | 3.7 |
| HDA (40%) | 24.8 | 24.8 | 2.9 | 4.0 |
| Reax 88B ® | 11.6 | 5.7 | 1.3 | 0.9 |
| Ethylene Glycol Stabilizer | 25.7 | 25.7 | 3.0 | 4.2 |
| Water | 476.0 | 234.0 | 55.3 | 38.2 |
| Total | 860.6 | 612.7 | 100.00 | 100.00 |

HDA is 1,6-hexanediamine.
Reax 88B ® is a sodium lignosulfonate.

TABLE 6

Average Particle Size of Microcapsules in Clomazone CS Formulations

| Formulation | Average Particle Size (μm) | Formulation | Average Particle Size (μm) |
|---|---|---|---|
| A | 26 | J | 11 |
| B | 21 | K | 17 |
| C | 16 | L | 14 |
| D | 18 | M | 2 |
| E | 15 | N | 9 |
| F | 15 | O | 7 |
| G | 23 | P | 14 |
| H | 12 | V | 21 |
| I | 12 | W | 17 |

Particle size was determined using a Malvern Master Sizer MS 20.

TABLE 7

Volatility of Clomazone from CS Formulations as Compared to the Volatility of Clomazone from the Standard, Command ® 4 EC Herbicide

| Formulation | Micrograms of Clomazone Collected | Percent of 4.0 EC |
|---|---|---|
| A | 28 | 32 |
| B | 30 | 33 |
| C | 17 | 19 |
| D | 20 | 22 |
| E | 8 | 8 |
| F | 9 | 10 |
| G | 15 | 14 |
| H | 13 | 14 |
| I | 21 | 15 |
| J | 23 | 17 |
| K | 24 | 17 |
| L | 81 | 91 |
| M | * | 110 |
| N | 56 | 62 |
| O | 22 | 16 |
| P | 14 | 14 |
| V | 110 | 103 |
| W | 126 | 114 |
| Standard 4.0 EC | 90–93 | 100 |

*Volatility determined by a different test method.

TABLE 8

Volatility Effect of Clomazone CS Formulations Compared to Command ® 4 EC Herbicide on Sunflowers in Field Studies

| Formulation (Test No.) | Area of Discolored Sunflowers (cm²) | Percent Reduction in Area Discolored by Volatility |
|---|---|---|
| A-1 (1) | 6578 | 49.0 |
| Command 4 EC | 12904 | |
| A-1 (2) | 17449 | 52.8 |
| Command 4 EC | 37004 | |
| P | 256334 | 67.5 |
| Command 4 EC | 788721 | |

TABLE 9

Relative Potency of Clomazone CS Formulations Compared to Command ® 4.EC Herbicide against Weed Species in Greenhouse Studies

| | Relative Potency | | | | | |
|---|---|---|---|---|---|---|
| Formulation | Barnyardgrass | Giant Foxtail | Yellow Foxtail | Shattercane | Green Foxtail | Velvetleaf |
| A | 0.70 | 0.54 | 0.35 | 0.66 | — | 0.69 |
| D | 0.50 | 0.59 | 1.02 | 0.40 | — | 0.36 |
| E | 0.19 | 0.28 | * | * | — | 0.34 |
| P | 0.63 | 0.54 | — | 0.95 | 0.95 | 0.90 |

*Too small to measure at rate tested.

TABLE 10

Efficacy of Clomazone CS Formulation A-1 Compared to Command ® 4 EC Herbicide against Weeds in Field Studies

| | Percent Control 15 DAE[1] and 30 DAE | | | | | | | |
|---|---|---|---|---|---|---|---|---|
| | Johnsongrass | | Bermudagrass | | Pitted Morningglory | | Sicklepod | |
| Formulation | 15 | 30 | 15 | 30 | 15 | 30 | 15 | 30 |
| A-1 | 68 | 54 | 0 | 1 | 72 | 54 | 26 | — |
| 4.0 EC | 85 | 56 | 20 | 55 | 66 | 70 | 21 | — |

| | Effects on Cotton | | | |
|---|---|---|---|---|
| | Percent Bleaching | | | |
| | 15 | 30 | Stand Reduction | Stunting |
| A-1 | 0.7 | 0.5 | none | none |
| 4.0 EC | 0.7 | 0.7 | none | none |

[1]DAE is days after emergence of the test plant species.
Rate of application is 1.0 pound a.i./acre.

TABLE 11

Efficacy of Clomazone CS Formulation E Compared to Command ® 4 EC Herbicide against Certain Weed Species in Field Studies

| | Percent Control Rate of Application (lb. ai/A)[1] | | | | | |
|---|---|---|---|---|---|---|
| Plant Species | 0.5 | | 0.25 | | 0.125 | |
| Formulation | E | 4 EC | E | 4 EC | E | 4 EC |
| Barnyardgrass | 100 | 100 | 98 | 99 | 91 | 97 |
| Giant Foxtail | 100 | 100 | 98 | 98 | 95 | 96 |
| Yellow Foxtail | 95 | 93 | 50 | 57 | 50 | 35 |

TABLE 11-continued

Efficacy of Clomazone CS Formulation E Compared to Command ® 4 EC Herbicide against Certain Weed Species in Field Studies

| Plant Species | Percent Control Rate of Application (lb. ai/A)[1] | | | | | |
|---|---|---|---|---|---|---|
| | 0.5 | | 0.25 | | 0.125 | |
| Formulation | E | 4 EC | E | 4 EC | E | 4 EC |
| Green Foxtail | 99 | 100 | 83 | 95 | 53 | 68 |
| Shattercane | 73 | 90 | 33 | 53 | 33 | 35 |
| Johnsongrass | 100 | 100 | 93 | 97 | 85 | 93 |
| Spring Wheat | 55 | 60 | 18 | 26 | 8 | 9 |
| Velvetleaf | 100 | 100 | 93 | 96 | 85 | 93 |
| Grass Average[2] | 95 | 97 | 77 | 83 | 68 | 71 |

[1]Formulations applied to the plots preemergence.
[2]Velvetleaf and Spring Wheat are not included in the grass average. Percent control ratings were determined 20 days after treatment.

TABLE 12

Efficacy of Clomazone CS Formulation P Compared to Command ® 4 EC Herbicide against Weeds in Field Studies

| Plant Species | Percent Control | | | | | |
|---|---|---|---|---|---|---|
| | 15 DAT | | 30 DAT | | 60 DAT | |
| Formulation | P | 4 EC | P | 4 EC | P | 4 EC |
| Velvetleaf | 95.0 | 95.0 | 97.5 | 97.55 | — | — |
| Prickly Sida | 89.3 | 90.5 | 83.6 | 90.7 | 77.3 | 88.5 |
| Spotted Spurge | — | — | 95.0 | 98.0 | — | — |
| Cocklebur | 58.8 | 72.5 | 58.8 | 59.4 | 87.5 | 93.5 |
| Broadleaf Signalgrass | 100.0 | 100.0 | 100.0 | 100.0 | 95.0 | 95.0 |
| Seedling Johnsongrass | — | — | 96.0 | 97.0 | — | — |
| Large Crabgrass | — | — | 95.5 | 99.0 | 100.0 | 100.0 |
| Pitted Morningglory | 93.0 | 95.2 | 82.9 | 89.5 | 78.4 | 88.5 |
| Ivyleaf Morningglory | 92.1 | 95.0 | 88.0 | 91.0 | 57.0 | 77.0 |
| Entire Morningglory | 73.9 | 70.9 | 73.9 | 71.6 | 66.9 | 73.0 |
| Morningglory Spp. | — | — | 95.7 | 99.3 | 99.0 | 99.0 |

| | Effects on Cotton (Percent) | | | | | |
|---|---|---|---|---|---|---|
| | 15 DAT | | 30 DAT | | 60 DAT | |
| Formulation | P | 4 EC | P | 4 EC | P | 4 EC |
| Stand Reduction | 0 | 0 | 0 | 0 | 0 | 0 |
| Stunting | 0.5 | 0.2 | 1.1 | 3.0 | 0 | 0 |
| Discoloration | 1.8 | 5.9 | 1.7 | 4.9 | 0 | 0.2 |

DAT is days after treatment.
Rate of application for both formulations is 0.88 pound a.i./acre.

TABLE 13

Efficacy of Clomazone CS Formulation P Compared to Command ® 4 EC Herbicide against Certain Weeds in Field Studies

| Plant Species | Percent Control Rate of Application (lb/A)[1] | | | | | | | |
|---|---|---|---|---|---|---|---|---|
| | 0.25 | | 0.50 | | 0.75 | | 1.00 | |
| Formulation | P | 4 EC | P | 4 EC | P | 4 EC | P | 4 EC |
| Redroot Pigweed | 73.8 | 88.8 | 92.3 | 97.5 | 100.0 | 100.0 | 100.0 | 100.0 |
| Velvetleaf | 85.0 | 88.8 | 91.0 | 98.3 | 97.0 | 99.8 | 98.8 | 100.0 |
| Common Barnyardgrass | 92.3 | 95.0 | 97.3 | 100.0 | 100.0 | 100.0 | 99.8 | 100.0 |
| Giant Foxtail | 92.5 | 96.3 | 98.0 | 100.0 | 100.0 | 100.0 | 100.0 | 100.0 |
| Shattercane | 65.0 | 73.8 | 76.3 | 96.0 | 91.3 | 97.3 | 94.5 | 100.0 |

[1]Formulations applied to plots preemergence.
Percent control ratings were determined 18 days after treatment.

We claim:

1. A process for the preparation of herbicidally effective formulations of clomazone having a volatility less than fifty percent of the volatility of an emusifiable concentrate of clomazone containing four pounds of clomazone per gallon of formulation which comprises microencapsulating the clomazone by interfacial polymerization by the steps of:

a) providing an aqueous phase containing 0.3 to 3.0 wt. % of one or more emulsifiers; optionally 0.02 to 0.20 wt. % of a xanthan gum viscosity modifier/stabilizer, and 0.1 to 1.0 wt. % of an antifoam agent;

b) providing a water immiscible phase consisting of clomazone, polymethylene polyphenyl isocyanate (PMPPI), and a hydrocarbon solvent; the weight ratio of clomazone to PMPPI being in the range of 1:1 to 6:1;

c) emulsifying the water immiscible phase in the aqueous phase, forming a dispersion of water immiscible droplets throughout the aqueous phase;

d) agitating the dispersion while adding thereto an aqueous solution of 15 to 100 weight percent of at least one polyfunctional amine selected from ethylenediamine (EDA), diethyltriamine (DETA), triethylenetetramine (TETA), and 1,6-hexanediamine (HDA), with the proviso that (EDA) is used only in a mixture, the weight ratio of polyfunctional amine to PMPPI being in the range of 0.1:1 to 1:1, thus forming microcapsules having a polyurea shell wall around the water immiscible droplets;

e) curing the microcapsules by continuing the agitation while heating the dispersion at a temperature in the range of 35° to 60° C. for a period of 3 to 10 hours to produce a formulation in which the average size of the microcapsules is in the range of 5 to 50 microns;

f) optionally adjusting the pH to between 6.5 and 9.0.

2. A process according to claim 1 in which the emulsifier is a polyvinyl alcohol; the antifoam agent is a polydimethyl siloxane; the ratio of clomazone to PMPPI is 4.5:1 to 4.7:1; the polyamine is a mixture of TETA and HDA in which the ratio of TETA to HDA is 3:1 to 1:3; the microcapsules are cured at 45° to 50° C. for 4 to 5 hours and have an average size of 5 to 30 microns.

3. A process of claim 2 in which there is added to the formulation after completion of the curing step one or more stabilizers selected from 0.05 to 0.30 wt. % xanthan gum, 0.75 to 6.5 wt. % propylene glycol, 0.5 to 6.0 wt. % one or more surfactants, and 0.25 to 0.50 wt. % smectite clay, to adjust the viscosity to 1700 to 3800 cps and the suspensibility to greater than 70%, each weight percent relative to the weight of the formulation after addition of the stabilizers.

4. A process according to claim 1 in which the emulsifier is a polyvinyl alcohol; the antifoam agent is a polydimethyl siloxane; the ratio of clomazone to PMPPI is 4.5:1 to 4.7:1; the polyamine is a mixture of DETA and HDA in which the ratio of DETA to HDA is 3:1 to 1:3; the microcapsules are cured at 45° to 50° C. for 4 to 5 hours and have an average size of 5 to 30 microns.

5. A process of claim 3 in which the amounts of stabilizers added are 0.05 to 0.25 xanthan gum and 1.0 to 6.0 propylene glycol.

6. A process according to claim 1 in which the emulsifiers are a polyvinyl alcohol and, optionally a sodium salt of sulfonated naphthalene condensate; the antifoam agent is a polydimethyl siloxane; the ratio of clomazone to PMPPI is 4.5:1 to 4.7:1; the polyamine is DETA, the microcapsules are cured at 45° to 50° C. for 4 to 5 hours and have an average size of 5 to 30 microns.

7. An herbicidal formulation prepared according to any one of claims 1 through 6.

8. A process for the preparation of herbicidally effective formulations of clomazone having a volatility less than fifty percent of the volatility of an emusifiable concentrate of clomazone containing four pounds of clomazone per gallon of formulation which comprises microencapsulating the clomazone by interfacial polymerization by the steps of:

a) providing an aqueous phase containing 0.5 to 3.0 wt. % of one or more emulsifiers; optionally 0.05 to 0.20 wt. % of a xanthan gum viscosity modifier/stabilizer, and 0.3 to 1.0 wt. % of an antifoam agent;

b) providing a water immiscible phase consisting of clomazone, polymethylene polyphenyl isocyanate (PMPPI), and a hydrocarbon solvent; the weight ratio of clomazone to PMPPI being in the range of 1:1 to 6:1;

c) emulsifying the water immiscible phase in the aqueous phase, forming a dispersion of water immiscible droplets throughout the aqueous phase;

d) agitating the dispersion while adding thereto at least one polyfunctional amine selected from diethyltriamine (DETA), triethylene-tetramine (TETA) and 1,6-hexanediamine (HDA), the weight ratio of polyfunctional amine to PMPPI being in the range of 0.1:1 to 1:1, thus forming microcapsules having a polyurea shell wall around the water immiscible droplets;

e) curing the microcapsules by continuing the agitation while heating the dispersion at a temperature in the range of 35° to 60° C. for a period of 3 to 10 hours;

f) optionally adjusting the pH to between 6.5 and 9.0.

9. An herbicidal composition containing from 1 to 4 pounds of clomazone per gallon of formulation and having a volatility less than fifty percent of the volatility of an emusifiable concentrate of clomazone containing four pounds of clomazone per gallon of formulation, comprising:

a) an aqueous suspension of microcapsules made up of a polyurea shell surrounding a core of clomazone and a minor amount of a hydrocarbon solvent, the polyurea having been formed from the interfacial reaction of polymethylene polyphenyl isocyanate (PMPPI) with ethylenediamine (EDA), diethylenetriamine (DETA), triethylenetetramine (TETA), or 1,6-hexanediamine (HDA), or a mixture of the polyfunctional amines, with the proviso that EDA is used only in a mixture;

b) 0.2 to 1.00 wt. % polyvinyl alcohol;

c) 0.1 to 0.5 wt. % antifoam agent;

d) optionally 0.07 to 0.30 wt. % xanthan gum viscosity modifier/stabilizer; and e) 0.75 to 7.0 wt. % propylene glycol, the average size of the microcapsules being in the range of 5 to 50 microns and having a suspensibility of greater than 70%, a viscosity of 1700 to 3800 cps, and a 100 mesh wet screen analysis of greater than 99.95%.

10. A composition of claim 9 containing two pounds of clomazone per gallon of formulation, in which the weight ratio of clomazone to PMPPI is 4.5:1 to 4.7:1 and the polyfunctional amines are TETA and HDA, with the weight ratio of TETA to HDA 3:1 to 1:3.

11. A composition of claim 9 containing two pounds of clomazone per gallon of formulation, in which the weight ratio of clomazone to PMPPI is 4.5:1 to 4.7:1 and the polyfunctional amines are TETA and DETA, with the weight ratio of TETA to DETA 3:1 to 1:3.

12. A composition of claim 9 containing two pounds of clomazone per gallon of formulation, in which the weight ratio of clomazone to PMPPI is 4.5:1 to 4.7:1 and the polyfunctional amines are DETA and HDA, with the weight ratio of DETA to HDA 3:1 to 1:3.

13. A composition of claim 9 containing three pounds of clomazone per gallon of formulation, in which the weight ratio of clomazone to PMPPI is 4.5:1 to 4.7:1 and the polyfunctional amine is DETA.

14. A composition of claim 13 in which the pH is adjusted to between 6.5 and 9.0.

* * * * *